(12) United States Patent
Al-Abed et al.

(10) Patent No.: US 6,538,131 B1
(45) Date of Patent: Mar. 25, 2003

(54) SYNTHETIC PROCESS FOR HIGHLY FUNCTIONALIZED CARBOCYCLIC POLYOLS AND SUBSTITUTED SUGAR ANALOGS

(75) Inventors: Yousef Al-Abed, Port Washington, NY (US); Mohindra Seepersaud, Richmond Hill, NY (US)

(73) Assignee: The Picower Institute for Medical Research, Manhasset, NY (US)

( * ) Notice: Subject to any disclaimer, the term of this patent is extended or adjusted under 35 U.S.C. 154(b) by 0 days.

(21) Appl. No.: 09/556,147

(22) Filed: Apr. 19, 2000

Related U.S. Application Data (60) Provisional application No. 60/130,049, filed on Apr. 19, 1999.

(51) Int. Cl.$^7$ .......................... C07G 17/00; C07H 1/00; C07H 3/00; C08B 37/00
(52) U.S. Cl. ...................... 536/124; 536/1.11
(58) Field of Search ........................... 435/7.1; 536/124, 536/1.11

(56) References Cited

PUBLICATIONS

Sillier et al. Tetrahedron Letters 40(4): 853–856 (Jan. 1999).*
Hasemann, C., et al., 1996, "The Crystal Structure of the Bifunctional Enzyme 6–Phosphofructo–2–Kinase/Fructose–2,6–Bisphosphatase Reveals Distinct Domain Homologies", Structure, vol. 4, pp. 1017–1029.
Pilkis, S.J., et al., 1995, "6–Phosphofructo–2–Kinase/Fructose–2,6–Bisphosphatase: A Metabolic Signaling Enzyme", Ann Rev. Biochem, vol. 64, pp. 799–835.
Rousseau, G.G., et al., 1993, "Mammalian 6–Phosphorfructo–2–Kinase/Fructose–2,6–Biophosphatase: A Bifunctional Enzyme That Controls Glycolsis", Nucl Acid Res Mol Biol, vol. 45, pp. 99–127.
Fürstner, A., et al., 1997, "Macrocycles by Ring–Closing Metathesis", Synthesis, pp. 792–803.
Grubbs, R.H., et al., 1995, "Ring–Closing Metathesis and Related Processes in Organic Synthesis", Acc Chem Res, vol. 28, pp. 446–452.
Meng, D., et al., 1997, "Total Syntheses of Epothilones A and B", J Am Chem Soc, vol. 119, pp. 10073–10092.
Crimmins, M.T., et al., 1997, "Asymmetric Aldol–Ring–Closing Metathesis Strategy for the Enantioselective Construction of Six– to Nine–Membered Oxygen Heterocycles", J Org Chem, vol. 62, pp. 7548–4549.
Schmalz, H., 1995 "Catalytic Ring–Closing Metathesis: A New, Powerful Technique for Carbon–Carbon Coupling in Organic Synthesis", Angew Chem Int Ed Engl., vol. 34, No. 17, pp. 1833–1836.

Arisawa, M., et al., 1997, "Synthesis of Chiral Bicyclic Lactams Using Ring Closure Metathesis: Synthesis of (–)–Coniceine and (S)–Pyrrolam A", SynLett, pp. 1179–1180.
Sellier, O., et al., 1999, "Ring Closing Metathesis as an Efficient Approach to Branched Cyclitols and Aminocyclitols: A Short Synthesis of Valiolamine", Tetrahedron Lett, vol. 40, pp. 853–856.
Ovaa, H., et al., 1998, "An Expeditious Route to the Synthesis of Highly Functionalized Chiral Oxepines frm Monosaccharides", Tetrahedron Lett, vol. 39, pp. 3025–3028.
Wilcox, C.S., et al., 1986, "New Approaches to Enzyme Regulators. Synthesis and Enzymological Activity of Carbocyclic Analogues of D–Fructofuranose and D–Fructofuranose 6–Phosphate", J Am Chem Soc, vol. 108, pp. 3102–3104.
Nathan, D.M., 1996, "The Pathophysiology of Diabetic Complications: How Much Does the Glucose Hypothesis Explain?", Ann Int Med, vol. 124, No. 1, Part 2, pp. 86–89.
Nishimura, M. et al., 1994, "Glucose–Stimulated Synthesis of Fructose 2,6–Bisphosphate in Rat Liver", J Biol Chem, vol. 269, No. 42, pp. 26100–26106.
Chesney, J., et al., 1999, "An Inducible Gene Product for 6–Phosphofructo–2–Kinase with an AU–Rich Instability Element: Role in Tumor Cell Glycosis and the Warburg Effect", Proc Natl Acad Sci USA, vol. 96, pp. 3047–3052.
Argilés, J.M., et al., 1988, "The Metabolic Environment of Cancer", J Mol Cell Biochem, vol. 81, pp. 3–17.
Hue, L., et al., 1993, "Fructose 2,6–Bisphosphate and the Control of Glycolysis By Growth Factors, Tumor Promoters and Oncogenes", Adv Enz Regul, vol. 33, pp. 97–110.
Freeman, F., et al., 1986, "Epimerization at C–2 during the Wittig Reaction of 2,3,5–tri–O–benzyl–D–Ribose and Methylidenetriphenylphosphorane", Carbohydr Res, vol. 154, pp. 270–274.
Seepersaud, M., et al. 1997, "C–6 Allylated Pyranosides for the Synthesis of Complex Oxygenated Tetrahydrofurans", Tetrahedron, vol. 53, No. 16, pp. 5711–5724.
Seepersaud, et al., 1999, "Total Synthesis of Carba–D–Fructofuranose Via a Novel Metathesis Reaction", Organic Letters, vol. 1, No. 9, pp. 1463–1465.

* cited by examiner

*Primary Examiner*—Padmashri Ponnaluri
*Assistant Examiner*—Tomas H F Friend
(74) *Attorney, Agent, or Firm*—Piper Rudnick, LLP; Steven B. Kelber (57) ABSTRACT

Chemical processes for more efficient synthesis of carbocyclic polyols and substituted sugar analogs are disclosed, together with a novel class of cyclopentene polyol intermediate products and anhydro derivatives thereof.

13 Claims, 5 Drawing Sheets carbocyclic D-fructofuranoside

2 fructose 2,6-bisphosphate

(a) BuLi (2.1 eq), CH₃PPh₃⁺Br⁻ (2.3 eq), THF, 0 °C to RT, 87%, (b) DMSO (5 eq.), Et₃N (10 eq.), (COCl)₂ (4.8 eq.), CH₂Cl₂, -78 °C to RT, 90%, (c) CH₂=CH₂MgBr (1M in THF, 3 eq.), THF, -78 °C to 0 °C 92%, (d) BnBr (3 eq.), NaH (2.9 eq) , Bu₄NI (0.1 eq), DMF 98%. (e) Grubb's catalyst (10 mol%), CH₂Cl₂, r.t., 3d, 35% (8), 49% (7). Schrock's catalyst (20 mmol%), CH₂Cl₂, r.t., 18h, 87% (8).

FIG. 3

Epoxidation via (i) Sharpless Assymmetric epoxidation Ti(OiPr)$_4$, TBHP, CH$_2$Cl$_2$(ii) Va(acac)$_2$, TBHP, (iii) MCPBA, CH$_2$Cl$_2$

FIG.4

(a) (i)TEMPO, NaOCl, CH$_2$Cl$_2$, 99% (ii) MeMgBr(3M in THF), THF, -78 °C to 0 °C, 97%, (iii) Ac$_2$O, DMAP, EtOAc, 97%, (iv) SOCl$_2$, Pyr, 95%, (b) (i)NaOMe, MeOH,99%,(ii) DMSO, (COCl)$_2$, Et$_3$N, 97%, (c)(i) CH$_2$=CH$_2$MgBr ((1.0M in THF, 2.9 eq). THF, -78 °C to 0 °C, 65%, (ii) BnBr (3 eq), NaH (2.9 eq), Bu$_4$NI (0.1 eq), DMF 98%, (d) Schrock's catalyst (32 mmol%), Hexane, reflux, 81%. (13).

FIG.5

SYNTHETIC PROCESS FOR HIGHLY FUNCTIONALIZED CARBOCYCLIC POLYOLS AND SUBSTITUTED SUGAR ANALOGS

This application claims priority from U.S. Provisional Application Ser. No. 60/130,049, filed Apr. 19,1999. The entirety of that provisional is incorporated herewith.

TECHNICAL FIELD OF THE INVENTION

The present invention provides synthetic processes for shorter and more efficient syntheses of functionalized carbocyclic (polyol) compounds and substituted sugar analogs including novel classes of cyclopentene and cyclohexene polyol intermediates and derivatives thereof.

BACKGROUND OF THE INVENTION

Figure 1:
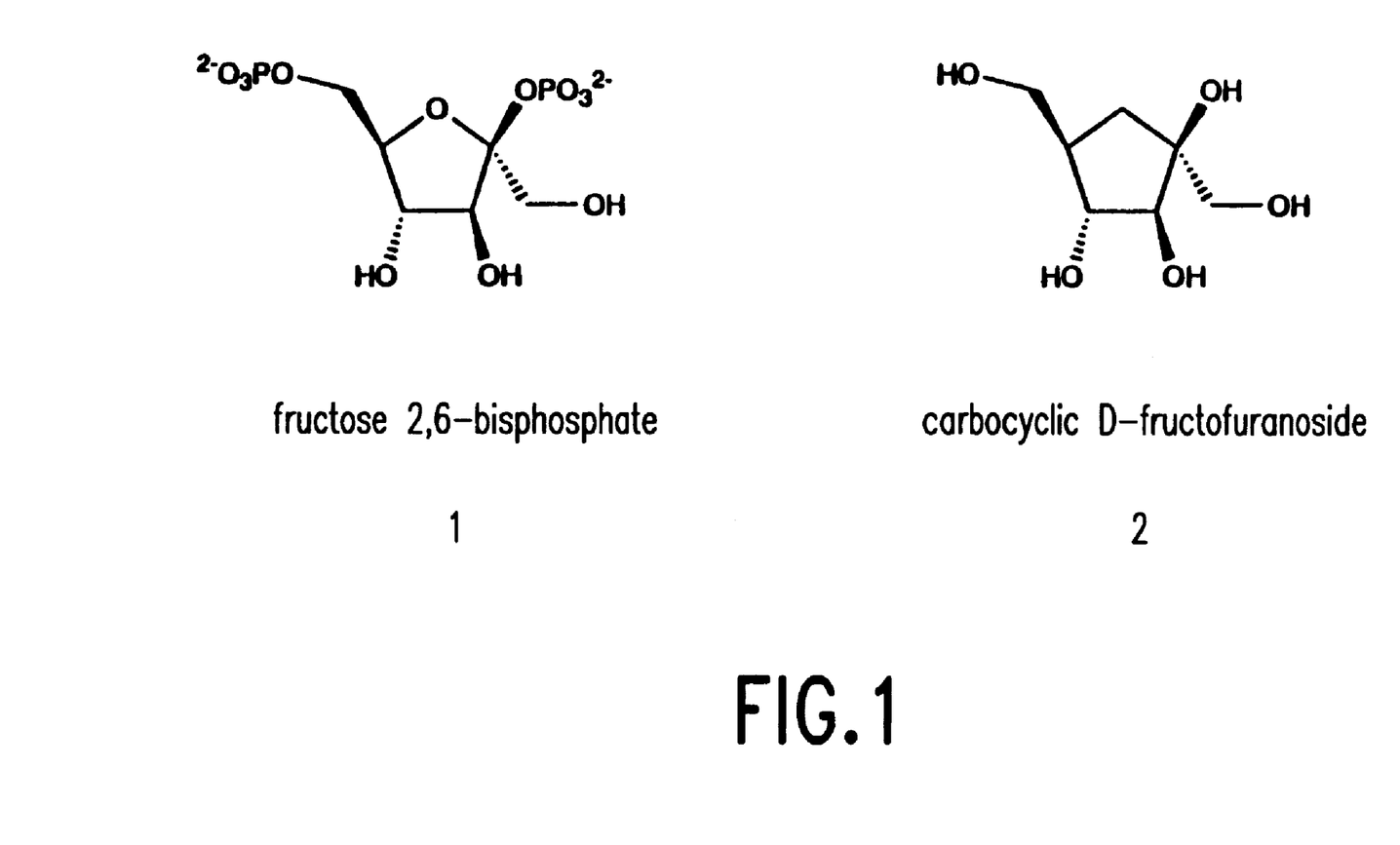
FIG. 1 shows the structure of fructose 2,6-bisphosphate (1) on the left and carbocyclic D-fructofuranoside (2) on the right.

Fructose 2,6-bisphosphate (FIG. 1, compound 1) is formed by phosphorylation of fructose 6-phosphate, a key substrate in the glycolysis pathway, in a reaction catalyzed by phosphofructokinases (PFK's) (Hasemann et al. *Structure*, 4:1017, 1996; Pilkis et al., *Ann. Rev. Biochem.* 64:799, 1995; and Rousseau et al., *Nucl. Acid Res. Mol. Biol.* 45:99, 1993). Fructose 2,6-bisphosphate is a key regulatory molecule for glycolysis and gluconeogenesis via its potent stimulatory effect on phosphofructokinase-1 activity and its inhibitory effect on fructose 1,6-bisphosphatase. The importance of this regulatory mechanism underscores the need for analogs of fructose 2,6-bisphosphate with which to probe and potentially control mechanisms that govern anaerobic glycolysis. To date, such controlled modulation of glycolysis has not been accomplished. In this regard, certain carbocyclic sugar analogs might be particularly useful. Accordingly, there is a need to generate carbocyclic sugar analogs efficiently, economically and in good yield.

Ring closing metathesis (RCM) has recently become a powerful tool for the synthesis of medium (5–8) to large (10–13 and higher) carbo or heterocycles (Furstner and Langemann, *Synthesis* 792, 1997; Grubbs and Miller, *Acc. Chem. Res.* 28: 446, 1995; Nicaloau et al., *J. Am. Chem. Soc.* 119:10073, 1997; Crimmins and Choy, *J. Org. Chem.* 62:7548, 1997; Schmalz, *Angew. Chem. Int. Ed. Engl.* 34:1833, 1995; and Arisawa et al., *Syn. Lett.* 1179, 1997). More recently there have been two reports dealing with RCM on functionalized substrates. The first is the synthesis of the six-membered poylsubstituted cyclohexene valiolamine employing Schrock's catalyst (Sellier et al., *Tetrahedron Lett.* 40:853, 1999) and the second is the synthesis of the seven-membered heterocyclic oxepine skeleton (Ovaa et al., *Tetrahedron Lett.* 39:3025, 1998) utilizing Grubbs' catalyst.

Carbocyclic D-fructofuranoside (FIG. 1, compound 2) has been synthesized in twelve-steps with cyclopentane ring closure achieved by free radical-mediated cyclization (Wilcox and Guadino, *J. Am. Chem. Soc.* 108:3102, 1986). This synthetic approach is difficult, provides low yields and is not useful for commercial synthesis. There is a need in the art to improve the synthesis of carbocyclic polyols and substituted analogs because such agents may be active in affecting intermediary metabolism (glycolysis).

SUMMARY OF THE INVENTION

By controlling glycolysis, it may be possible to interfere with some diseases that manifest aberrant activity or flux in glycolytic pathways. Such diseases would include, for instance, insulin-dependent and non-insulin dependent diabetes mellitus (Nathan, *Ann. Int. Med.* 124:86, 1996; and Nishimura et al., *J. Biol. Chem.* 269:26100, 1994) and cancer (Chesney et al., *Proc. Natl. Acad. Sci. USA* 6:3046, 1999; Argiles et al., *J. Mol. Cell. Biochem.* 81:3, 1988; and Hue et al., *Adv. Enz. Regul.* 33:97, 1993). Unlike native carbohydrates such as phosphorylated fructose, carbocyclic sugar analogs cannot be metabolized and may therefore have prolonged effects on the control of glycolysis, offering the opportunity to interfere with or modulate both normal and pathological mechanisms that regulate glycolysis.

The present invention provides an improved process for synthesis of carbocyclic sugar analogs by annulation of an olefinic intermediate. One embodiment of the inventive process provides an eight-step synthesis procedure that is a significant improvement over a twelve-step process published in 1986. Specifically, one embodiment of the invention provides a process (according to Scheme I) for synthesizing a class of desired intermediate products for further derivatization to provide final carbocyclic sugar analogs, comprising the steps of:

(a) subjecting a pentose or a hexafuranose precursor compound that is not protected at the anomeric hydroxyl group to a Wittig reaction to effect ring opening and generate an alkene intermediate product;

(b) oxidizing the alkene intermediate product of step (a) to yield a keto-alkene intermediate product;

(c) effecting the nucleophilic addition of vinyl carbanion to the keto-alkene intermediate product of step (b) under Grignard conditions to provide a 1,6-heptadiene product;

(d) optionally protecting the generated free alcohol of the 1,6-heptadiene product of step (c) to generate a fully protected 1,6-heptadiene product;

(e) subjecting the 1,6-heptadiene product of step (c) or step (d) to ring closure metathesis (RCM) conditions with an RCM catalyst to effect ring closure and generate a functionalized cyclopentene product.

Figure 2:
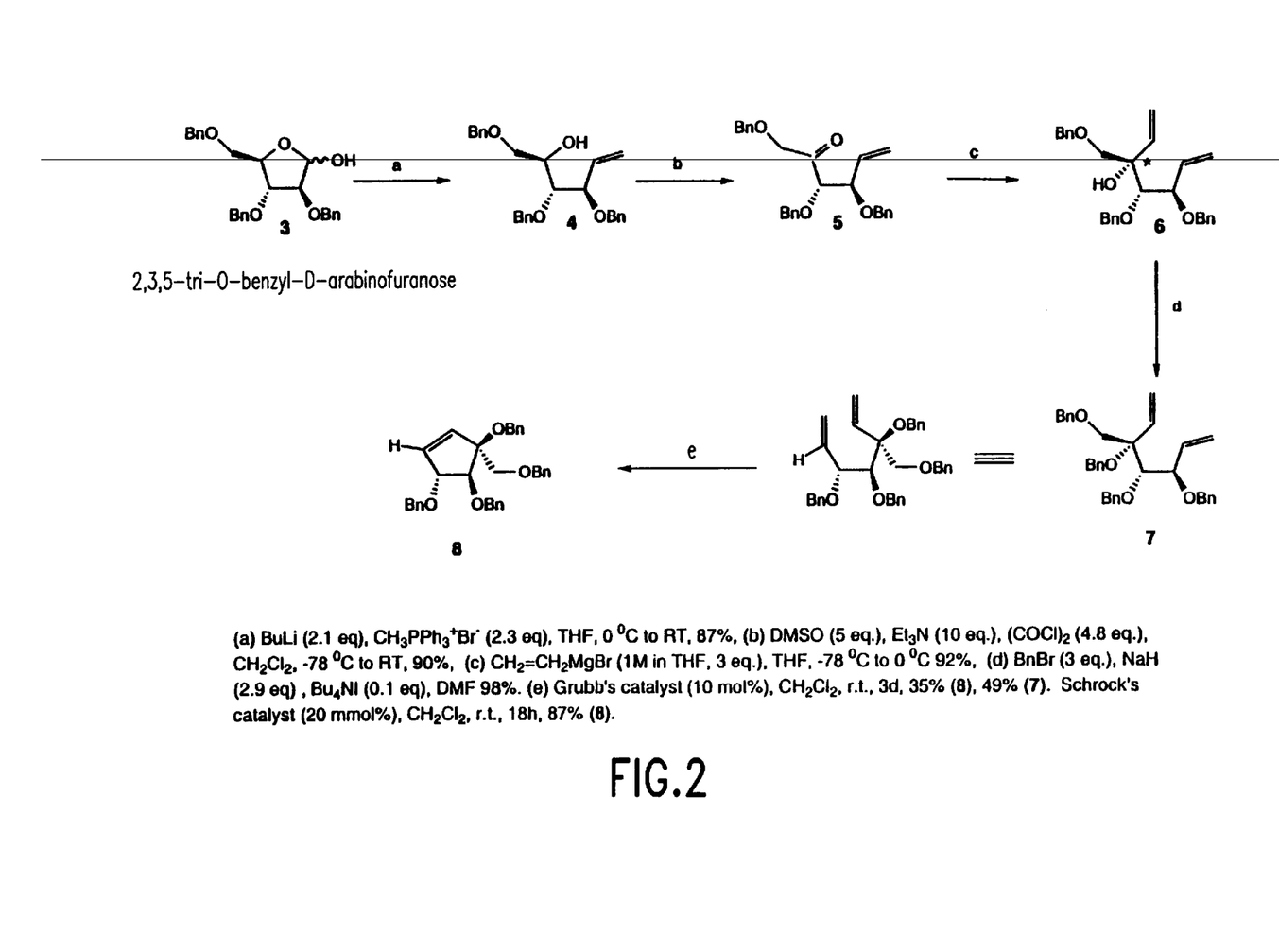
FIG. 2 shows a scheme (Scheme I) using a ring closing metathesis (RCM) method for the synthesis of functionalized cyclopentene intermediate products adapted for further derivatization to generate carbocyclic sugar analogs and related polyols.
Figure 3:
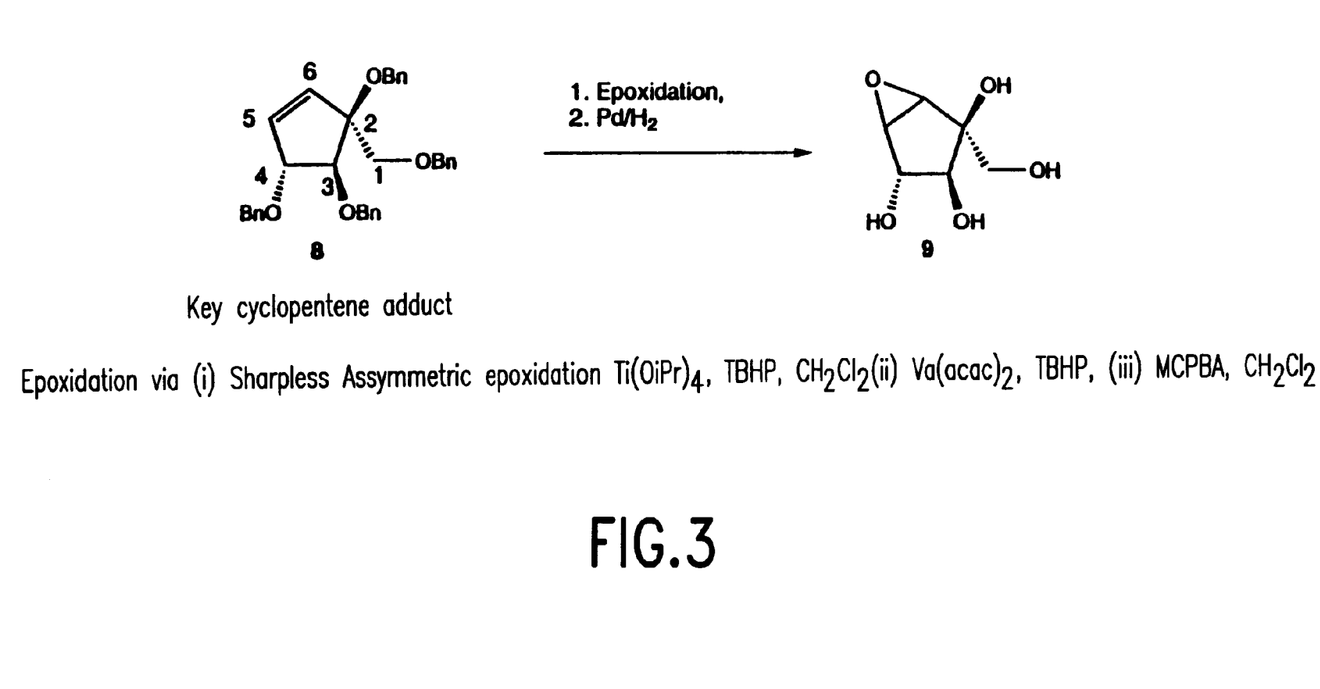
FIG. 3 shows a scheme for synthesis of functionalized anhydro cyclopentane intermediate products from the corresponding functionalized cyclopentene intermediate products shown in FIG. 2.

This synthetic scheme is (Scheme I) summarized in FIG. 2. The novel functionalized cyclopentene product of step (e) may then be deprotected and/or further functionalized or elaborated to provide carbocyclic sugar analog agents to probe, characterize and modulate glycolysis and the normal and pathological mechanisms that operate to control glycolysis in healthy and diseased individuals. For example, the functionalized cyclopentene product of step (e) is subjected to Sharpless epoxidation to provide a corresponding anhydro cyclopentane product advantageous for the generation of carbocyclic sugar analogs (FIG. 3).

Figure 4:
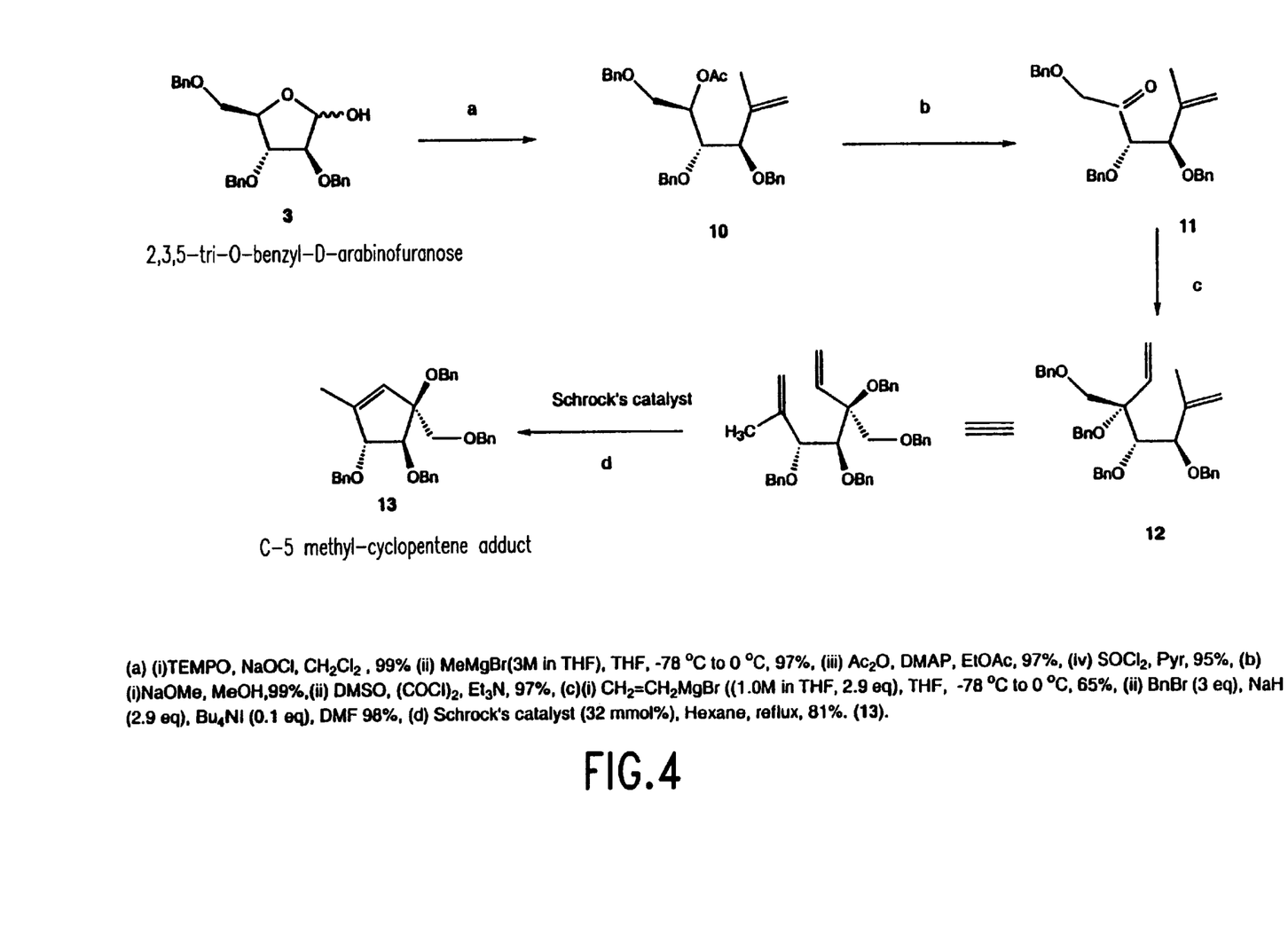
FIG. 4 shows a scheme (Scheme I) using a ring closing metathesis (RCM) method for synthesis of methyl-substituted functionalized cyclopentene intermediate products adapted for further derivatization to generate carbocyclic sugar analogs and related polyols.

Alternatively, at step (a), a series of reactions including sequential oxidation, methyl Grignard addition and acetylation followed by thionyl chloride elimination, optionally executed as a one-pot reaction, (according to Scheme II) may be substituted for the Wittig reaction to effect ring opening and generate an alkene intermediate product (see FIG. 4).

In a second alternative, a hexopyranose precursor compound is instead utilized at step (a) of Scheme I, and after step (b), the keto-alkene intermediate product is subjected to a Wittig reaction to provide a 1,6 heptadiene product that is suitable for step (e).

Figure 5:
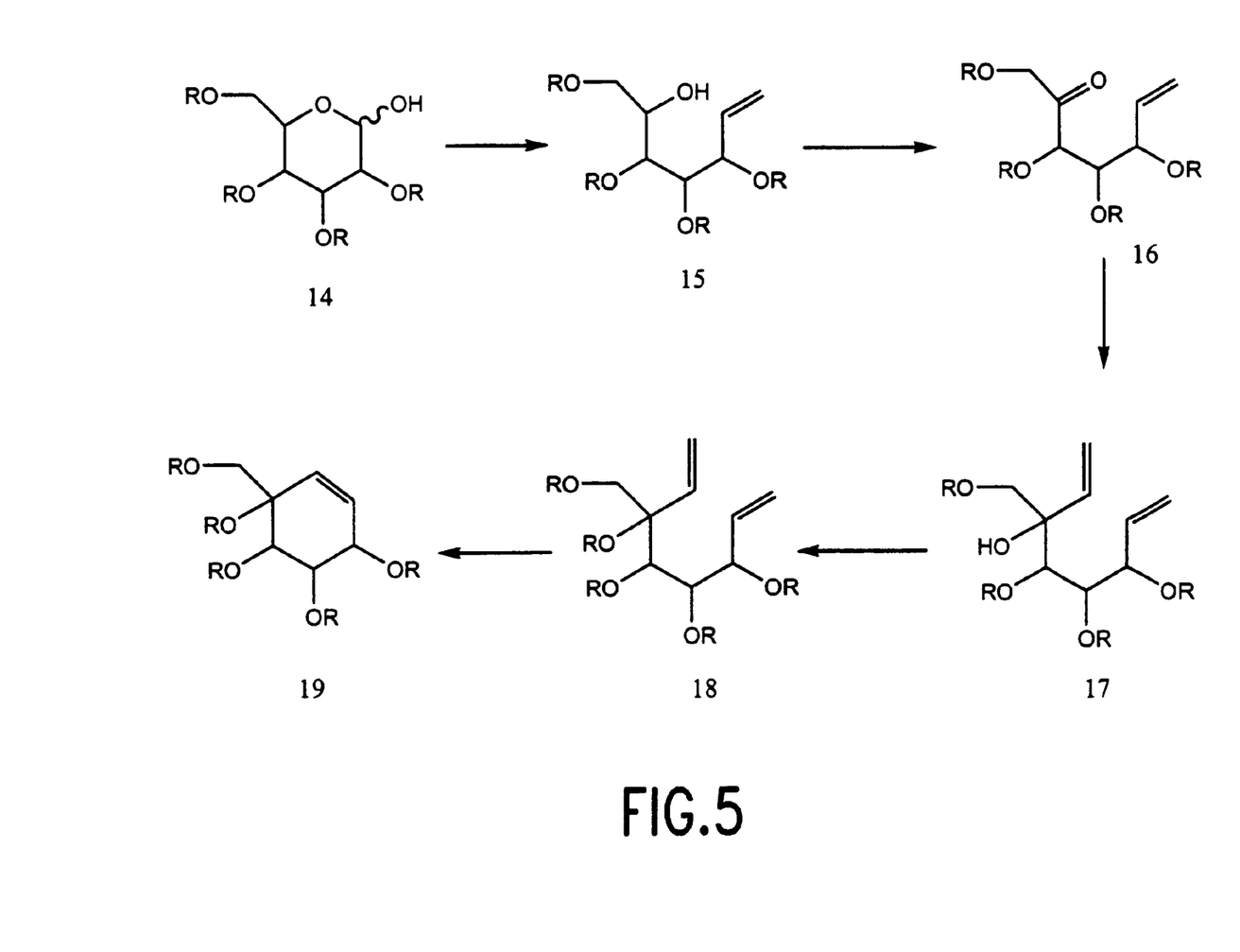
FIG. 5 shows a scheme (Scheme III) using a ring closing metathesis (RCM) method for synthesis of functionalized cyclohexene intermediate products adapted for further elaboration to generate carbocyclic sugar analogs and related compounds.

In a further embodiment of the general method (see FIG. 5), a hexopyranose precursor compound is utilized instead at step (a) of Scheme I, to provide a 1,7 octadiene intermediate product at step (c), such that the process provides a corresponding functionalized cyclohexene product (according to Scheme III, FIG. 5):

(a) subjecting a hexopyranose precursor compound (14) that is not protected at the anomeric hydroxyl group to a Wittig reaction to effect ring opening and generate an alkene intermediate product (15);

(b) oxidizing the alkene intermediate product of step (a), 15, to yield a keto-alkene intermediate product (16);

(c) effecting the nucleophilic addition of vinyl carbanion to the keto-alkene intermediate product of step (b), 16, under Grignard conditions to provide a 1,7-octadiene product (17);

(d) optionally protecting the generated free alcohol of the 1.7-octadiene product of step (c) to generate a fully protected 1,7-octadiene product (18);

(e) subjecting the 1,7-octadiene product of step (c), 17, or step (d), 18, to ring closure metathesis (RCM) conditions with an RCM catalyst to effect ring closure and generate a functionalized cyclohexene product (19).

Any of the functionalized cyclopentene or cyclohexene products of step (e), from Scheme I, II, or III, are converted into corresponding carbacyclic sugar analogs. In some cases, this is accomplished by carbonylation (hydroformylation) followed by reduction, as described in detail in Example 9 and Scheme V with completion in Scheme VI, a process not previously demonstrated on highly functionalized polyol (i.e., polyhydroxylated) systems. Alternatively, the starting materials can be halo-sugars or azo-sugars. Preferably, any of the RCM catalysts above are selected from the group consisting of a Grubbs' catalyst and a Schrock's catalyst. More preferably, the protecting groups are benzyl or alkyl-silyl groups, and combinations thereof. Still more preferably, the pentose precursor compound is 2,3,5-tri-O-benzyl-D-arabinofuranose.

DETAILED DESCRIPTION OF THE INVENTION

Wilcox and Guadino (*J. Am. Chem. Soc.* 108:3102, 1986) have shown the first and only synthetic approach to carbocyclic D-fructofuranoside. The overall synthesis involved 12 steps. The cyclopentane ring closure was done via a free radical-mediated cyclization. The present invention provides a new and advantageous process for synthesis of carbocyclic sugar analogs by annulation of an olefinic intermediate via ring closing metathesis. In particular, we describe herein the synthesis of a polyhydroxylated cyclopentene, carbafructo-furanose precursor (compound 8 in FIG. 2) using RCM methodology. In this synthetic approach shown in FIG. 2, compound 8 arises via RCM of a diene precursor, compound 7, which is readily assembled from an available carbohydrate derivative (compound 3 in FIG. 2).

Treatment of the commercially available 2,3,5-tri-O-benzyl-D-arabinofuranose (Freeman and Robarge, *Carbohydr. Res.* 154:270, 1986) (see FIG. 2, compound 3) under Wittig and Swem conditions (briefly, BuLi (2.1 eq.), $CH_3PPh_3^+Br^-$ (2.3 eq.), THF, 0° C. to RT, 87%, and the DMSO (5 eq.), $Et_3N$ (10 eq.), $(COCl)_2$ (4.8 eq.), $CH_2Cl_2$, –78° C. to RT 90%) furn 5 in 78% yield. Addition of vinylmagnesiumbromide (briefly $CH_2$=$CH_2MgBr$ (1M in THF, 3 eq.), THF, –78° C. to 0° C., 92%) afforded the single diene alcohol precursor (FIG. 4, compound 6). The origin of the stereochemistry at this center cannot be readily predicted and is probably a result of the stereo-directing effect of the chiral α-benzyloxy group. The alcohol (compound 6) was subsequently protected as the benzyl ether (compound 7 of FIG. 2; briefly BNBr (3 eq.), $Bu_4NI$ (0.1 eq.), DMF 98%) and then subjected to RCM under Schrock's conditions (briefly, Schrock's catalyst (20 mmol %), $CH_2Cl_2$, RT, 87%) yielding the novel functionalized cyclopentene intermediate product (compound 8 in FIG. 2).

The stereochemistry of the cyclic product was established using nuclear Overhauser effect (NOE) analysis. NOE analysis has previously been used in the structural assignment of similar five- and six-membered cyclic compounds (Sellier et al., *Tetrahedron Lett.* 40:853, 1999; and Seepersaud et al., *Tetrahedron* 53:5711, 1997). The IH NMR signals of compound 8 were first identified by correlated spectroscopy (COSY). The NOE analysis allowed for structural assignment. An NOE of 1.5% between $H_3$ and one of the benzylic protons $H_1$ and also a 1.0% NOE between $H_6$ and the other benzylic proton $H_1$ was observed. These data provide strong support for a syn relationship between C-2/C-3 benzyloxy groups and assigns the framework of compound 8 with the correct stereochemistry at C-2, 3 and C-4 of compound 1 (FIG. 1) since the stereochemistry at C-3 and C-4 was conserved.

Note the protecting groups utilized according to the teachings herein may be chosen from among the many that are well-known in the chemical arts, such as benzyl, alkylsilyl, benzoyl, and acetyl.

In summary we have demonstrated concise and efficient syntheses of functionalized cyclopentene and cyclohexene products, via a pathway that is generalized to a variety of starting pentoses and hexoses, to provide highly functionalized cyclic products. These functionalized cyclohexene and cyclopentene products, together with corresponding methyl-substituted and anhydro derivatives thereof, are themselves precursors adapted for subsequent derivatization or other elaboration to provide useful carbocyclic sugar analogs and related polyol compounds. A new approach comprising hydroformylation of the functionalized cycloalkenes generated as above, followed by reduction, yields the final carbocyclic sugar analogs and other carbacyclic polyol products in fewer steps than heretofor possible.

EXAMPLE 1

This example illustrates the synthesis of compound 4 (FIG. 2) from 2,3,5-tri-O-benzyl-D-arabinofuranose (compound 3, FIG. 2). For the following syntheses, thin layer chromatography (TLC) was carried out on aluminum sheets precoated with silica gel 60 (HF-254, E. Merck) to a thickness of 0.25 mm. Flash column chromatography (FCC) was performed using Kieselgel 60 (230–400 mesh, E. Merck) and usually employed a stepwise solvent polarity gradient, correlated with TLC mobility. $^1$H and $^3$C NMR spectra were obtained on JEOL 270 instrument. Unless otherwise noted, spectra were recorded at 270 and 67.5 MHz respectively. Mass spectral analyses were performed by mass spectrometral facilities of Hunter College and University of Illinois. Dry THF was obtained by distillation, under nitrogen from potassium-benzophenon ketyl. Dichloromethane was distilled from $P_2O_5$. Other solvents were purified and dried by using standard procedures.

nBuLi (11.0 mmole, 1.6 M in Hexane) was added to a suspension of methyl triphenylphosphonium bromide (4.28 g, 12.0 mmol) in dry THF (25 mL) at 0° C. under $N_2$. The suspension was allowed to stir for 30 min at 0° C. then warmed up to RT (1 h). 2,3,5-tri-O-benzyl-D-arabinofuranos (compound 3; 2.0 g, 5 mmol) was dissolved in THF (5 mL) and transferred by cannula dropwise over 10 min. The reaction mixture was allowed to warm to RT, followed by addition of $Et_2O$ (100 mL). The suspension was filtered through celite and excess solvent evaporated. FCC (10%–30% EtOAc: PE) furnished a clear oil, compound 4 of FIG. 2 (1.81 g, 87%). Rf 0.6 (20% EtOAc:PE); $^1$H NMR (270 MHz, $CDCl_3$) δ7.34 (m, 15H), 5.95 (m, 1H), 5.34 (m, 2H), 4.62 (ABq, Δδ=0.09 ppm, 2H, J=11.9 Hz), 4.52 (m, 2H), 4.50 (ABq, Δδ=0.23 ppm, 2H, J=11.2 Hz), 4.1 (m, 1H), 4.04 (m, 1H), 3.64 (m, 3H). $^{13}$C NMR (67.5 MHz, $CDCl_3$) δ138.3, 138.2, 138.0, 135.2, 128.5–127.8 (8 signals), 119.2, 80.6, 74.2, 73.5, 71.0, 70.8, 70.5.

EXAMPLE 2

This example illustrates the synthesis of compound 5 from compound 4 (see FIG. 2). To a solution of oxalyl chloride (549 mg, 4.3 mmol) in anhydrous $CH_2Cl_2$ (5 mL) at −78° C. under $N_2$ was added DMSO (375 mg, 4.8 mmol) and the mixture allowed to stir for 20 min. The alcohol, compound 4, [200 mg, 0.48 mmol, dissolved in $CH_2Cl_2$ (4 mL)] was then added and the reaction allowed to stir for 25 min. $Et_3N$ (847 mg, 8.6 mmol) was then added and the solution warmed to 0° C. $Et_2O$ (50 mL) was added and the combined organic washed with saturated aqueous $NaHCO_3$ (30 mL), brine (30 mL) and dried ($MgSO_4$). The $Et_2O$ extract was concentrated in vacuo and purified by FCC (10–40% EtOAc:PE), to give the ketone, compound 5 (179 mg, 90%). Rf 0.75 (25% EtOAc:PE); $^1$H NMR (270 MHz, $CDCl_3$) δ7.30 (m, 15H), 5.91 (m, 1H), 5.33 (m, 1H), 4.48–4.60 (m, 4H), 4.35 (m, 2H), 4.28 (m, 2H), 4.19 (m, 1H), 4.00 (d, 1H, J=3.5 Hz) $^{13}$C NMR (67.5 MHz, $CDCl_3$) δ207.7, 137.6, 137.5, 136.9, 134.2, 128.6–127–8 (6 signals), 119.9, 85.9, 81.0, 74.7, 73.4, 71.0.

MS (ES) m/z 439 (M+Na$^+$), 434.2 (M+NH4$^+$), 181 (base peak).

EXAMPLE 3

This example illustrates the synthesis of compound 6 from compound 5 (as shown in FIG. 2). The azeotropically dried ketone (compound 5; 190 mg, 0.5 mmol) intermediate was dissolved in THF (5 mL), then cooled to −78° C. A 1 M solution of vinylmagnesiumbromide (1.40 mmol, 1.4 mL) was then added dropwise and the solution was allowed to warm up to 0° C. The reaction was quenched by addition to cold saturated $NH_4Cl$ (15 mL). The mixture was extracted with $Et_2O$ (3×20 mL), washed with saturated aqueous $NaHCO_3$ (30 mL), brine (30 mL) and dried ($MgSO_4$). The $Et_2O$ extract was concentrated in vacuo and purified by FCC (20–60% EtOAc:PE) to give the alcohol, compound 6 of FIG. 2 (204 mg, 92%). Rf 0.4 (10% EtOAc:PE); $^1$H NMR (270 MHz, $CDCl_3$) δ7.32 (m, 15H), 6.17 (dd, 1H, J=1.7, 17.3 Hz), 5.99 (m, 1H), 5.45 (dd, 1H, J=1.7, 17.3 Hz), 5.3 (m, 2H), 5.17 (dd, 1H, J=1.7, 10.6 Hz), 4.67 (ABq, Δδ=0.07 ppm, 2H, J=11.1 Hz), 4.42 (ABq, Δδ=0.34 ppm, 2H, J=11.4 Hz), 4.45 (m, 2H), 4.18 (dd, 1H, J=2.2, 8.2 Hz), 3.72 (d, 1H, J=2.2 Hz), 3.79 (d, 1H, J=8.4 Hz), 3.25 (d, 1H, J=8.4 Hz). $^{13}$C NMR (67.5 MHz, $CDCl_3$) δ140.3, 138.2, 138.1, 137.3, 136.1, 128.7–127.7 (7 signals), 118.9, 114.5, 82.0, 81.6, 78.3, 76.0, 74.4, 73.5, 70.6.

MS (ES) m/z 467 (M+Na$^+$), 181 (base peak).

EXAMPLE 4

This example illustrates the synthesis of compound 7 from compound 6 (as shown in FIG. 2). The alcohol intermediate (compound 6) (80 mg, 0.18 mmol) was dissolved in DMF (3 mL, anhydrous) and the solution was cooled to 0° C. and NaH (35 mg, 0.88 mmol) was added. $Bu_4NI$ (13 mg, 0.036 mmol) followed by BnBr (156 mg, 0.9 mmol) was then added and the reaction mixture allowed to stir for 30 min. The reaction was quenched by dropwise addition of MeOH (2 mL), then water (15 mL) and the aqueous mixture was extracted with $Et_2O$ (3×15 mL). The combined $Et_2O$ extract was washed with saturated aqueous $NaHCO_3$ (10 mL), brine (10 mL) and excess solvent evaporated to give the tetrabenzylated product, compound 7 of FIG. 2 (94 mg, 98%). Rf 0.7 (10% EtOAc:PE); $^1$H NMR (270 MHz, $CDCl_3$) δ7.33 (m, 20H), 6.08 (dd, 1H, J=10.6, 18.0 Hz), 6.01 (m, 1H), 5.34 (d, 1H, J=1.7 Hz), 5.28 (m, 2H), 5.22 (m, 1H), 4.74 (ABq, Δδ=0.08 ppm, 2H, J=11.1 Hz), 4.53 (ABq, Δδ=0.11 ppm, 2H, J=11.6 Hz), 4.4 (ABq, Δδ=0.36 ppm, 2H, J=11.9 Hz), 4.34 (m, 2H), 4.11 (dd, 1H, J=3.0, 7.7 Hz), 3.82 (d, 1H, J=10.9 Hz), 3.76 (d, 1H, J=3.2 Hz), 3.52 (d, 1H, J=10.9 Hz). $^{13}$C NMR (67.5 MHz, $CDCl_3$) δ6 139.8, 138.9, 138.2, 138.1, 137.3, 137.2, 128.5–127.0 (9 signals), 117.7, 116.1, 86.7, 82.8, 79.8, 76.3, 73.3, 70.2, 70.1, 65.1.

MS (ES) m/z 557 [(M+Na$^+$), (base peak)], 535 (M+H$^+$).

EXAMPLE 5

This example illustrates the synthesis of compound 8 from compound 7 using RCM under Schrock's conditions (see FIG. 2). The diene, compound 7, (70 mg, 0.131 mmol) dissolved in anhydrous $CH_2Cl_2$ (1.0 mL) was added to a homogeneous orange-red solution of Schrock's catalyst 2,6-diisopropylphenylimido neophylidenemolybdenum (VI) bis (hexafluoro-t-butoxide) (20 mg, 0.026 mmol) in anhydrous $CH_2Cl_2$ (4 mL) under $N_2$. The resulting mixture was stirred at 20° C. for 18 h, at which time TLC showed formation of new material. The reaction mixture was quenched by exposure to air for 2 h then excess solvent evaporated in vacuo. The brown residue was purified by FCC (5–10% EtOAc:PE) to give the alkene, compound 8 (57.6 mg, 87%). %). Rf 0.5 (10% EtOAc:PE); $^1$H NMR (270 MHz, $CDCl_3$) δ7.25 (m, 20H), 6.05 (d, 1H, J=6.0 Hz, H−5), 5.77 (d, 1H, J=6.0 Hz, H−6), 4.78 (m, 1H), 4.70 (m, 1H, H−4), 4.56–4.46 (m, 6H), 4.34 (m, 1H), 4.05 (d, 1H, J=4.0 Hz, H−3), 3.57 (ABq, Δδ=0.07 ppm, 2H, J=9.5 Hz, H−1) $^{13}$C NMR (67.5 MHz, $CDCl_3$) δ6 139.5, 138.7, 138.4, 138.3, 135.5, 134.0, 128.5–126.2 (8 signals), 89.1, 87.5, 84.7, 75.0, 73.6, 72.8, 71.6, 67.2.

HRMS (FABMS) Calculated for $C_{34}H_{34}\ O_4$ (M+H$^+$) 507.253535, found 507.253500.

EXAMPLE 6

This example illustrates an alternative synthesis of compound 8 from compound 7 using RCM under Grubbs' conditions. The diene (compound 7) (40 mg, 0.075 mmol) was dissolved in anhydrous $CH_2Cl_2$ (1.0 mL) and was added to a homogeneous orange-red solution of bis(tricyclopentylphosphine)benzylidine ruthenium dichloride (6.2 mg, 0.075 mmol) in anhydrous $CH_2Cl_2$ (2.5 mL) under $N_2$. The resulting mixture was stirred at 20° C. for 48 h, at which time TLC showed formation of new material. The reaction mixture was quenched by exposure to air for 2 h then excess solvent evaporated in vacuo. The black residue was purified by FCC (5–10% EtOAc:PE) to give the diene (19.6 mg, 49%) and the carbafructofuranose precursor, compound 8, (13.3 mg, 35%). Rf 0.5 (10% EtOAc:PE); $^1$H NMR (270 MHz, $CDCl_3$) δ6 7.25 (m, 20H), 6.05 (d, 1H, J=6.0 Hz, H–5), 5.77 (d, 1H, J=6.0 Hz, H–6), 4.78 (m, 1H), 4.70 (m, 1H, H–4), 4.56–4.46 (m, 6H), 4.34 (m, 1H), 4.05 (d, 1H, J=4.0 Hz, H–3), 3.57 (ABq, Δδ=0.07 ppm, 2H, J=9.5 Hz, H–1). $^{13}$C NMR (67.5 MHz, $CDCl_3$) δ6 139.5, 138.7, 138.4, 138.3, 135.5, 134.0, 128.5–126.2 (8 signals), 89.1, 87.5, 84.7, 75.0, 73.6, 72.8, 71.6, 67.2.

HRMS (FABMS) Calculated for $C_{34}H_{34}O_4$ $(M+H^+)$ 507.253535, found 507.253500.

EXAMPLE 7

This example illustrates the synthesis of a class of methyl-substituted cyclopentene intermediate products (compound 13, FIG. 4), beginning with the same starting material (compound 3) as above. The synthetic scheme shown in FIG. 4 replaces the Wittig reaction of step a in FIG. 2 with a series of reactions including sequential oxidation, methyl Grignard addition and acetylation followed by thionyl chloride elimination (optionally executed as a one-pot reaction) to effect ring opening and generate an alkene intermediate product, compound 10 (see FIG. 4). Briefly, the one-pot reaction involved oxidation of the 2,3,5-tri-O-benzyl-D-arabinofuranose starting material with 2,2,6,6-tetramethyl-1-piperidinyloxy free radical (TEMPO), methyl Grignard addition and acetylation followed by thionyl chloride elimination under standard conditions to furnish the diene, compound 10 in 88% yield. Deacetylation followed by oxidation under conditions described for the analogous step in the scheme of FIG. 2, afforded the ketone, compound 11 in 96% yield. Addition of vinylmagnesiumbromide (as per scheme in FIG. 2) afforded the single diene alcohol precursor that was subsequently benzylated to provide compound 12 (FIG. 4). A single stereoisomer was obtained as in the above-described synthesis (FIG. 2). The benzyl ether was then subjected to RCM conditions. Briefly, the diene, compound 12 (45 mg, 0.082 mmol) dissolved in anhydrous hexane (1.0 mL) was added to a homogeneous orange-red solution of Schrock's catalyst 2,6-diisopropylphenylimido neophylidenemolybdenum (VI) bis(hexafluoro-t-butoxide) (20 mg, 0.026 mmol) in anhydrous hexane (3 mL) under $N_2$. The resulting mixture was refluxed at 90° C. for 18 h, at which time TLC showed formation of new material. The reaction mixture was quenched by exposure to air for 2 h then excess solvent evaporated in vacuo. The brown residue was purified by FCC (5–10% EtOAc:PE) to give the alkene, compound 13 (34 mg, 81%).

EXAMPLE 8

The above-described novel application of RCM methodology to highly functionalized substrates was additionally employed in the total synthesis of carbacyclic D-fructofuranoside, in which the fully protected 1,6 heptadiene product of step (d) in Scheme II (compound 12) was oxidized by selenium oxide ($SeO_2$) and tert-butyl hydrogen peroxide (TBHP) to produce the corresponding alcohol. Following benzyl protection, the fully protected 1,6 heptadiene product was subjected to RCM to effect ring closure and generate the functionalized cyclopentene product. Deprotection and hydrogenation of the olefin in the presence of hydrogen and palladium provided the desired carbacyclic D-fructofuranoside in 11 steps in overall yield of 45% from the 2,3,5-tri-O-benzyl-D-arabinofuranose starting material (compound 3, FIG. 2). (Seepersaud and A1-Abed, *Organic Letters* 1:1463–1465, 1999).

EXAMPLE 9

To shorten the synthesis and improve the yield of the desired carbacyclic D-fructofuranoside from the 2,3,5-tri-O-benzyl-D-arabinofuranose starting material (11 steps in overall yield of 45%; Example 8 above), we employed carbonylation methods not previously thought to be compatible with highly functionalized polyol systems. To provide a more efficient synthesis of carbafructofuranose (compound 2) involving fewer steps, we chose the cyclopentene (compound 8) as an attractive starting point because it possessed all the required functionality except at the C-5 position. What was needed was a one C extension at C-5 to give the hydroxymethyl group. Our strategy would also facilitate selective phosphorylation of C-2/C-6 to resemble the F2,6 BP target (compound 2), differentiating between the conserved protected hydroxyl groups and those generated by the hydroformylation (Scheme IV).

Scheme IV

Hydroformylation reactions on simple terminal and partially functionalized substrates have been well investigated, but there have been no reported examples of formylation on polyhydroxylated cyclic substrates. Carbonylation was accomplished according to Scheme V:

Scheme V

The hydroformylation reaction was carried out utilizing Wilkinson's catalyst [(Ph$_3$P)$_3$RhCl] in a mixture of carbon monoxide (40 bar) and hydrogen (40 bar) at 80° C. for 24 h. Under these reaction conditions the functionalized cyclopentene was converted quantitatively to the corresponding aldehyde.

The mixture of aldehydes (compounds 20 and 21) was then treated under reducing conditions (NaBH$_4$/MeOH) to furnish the corresponding alcohols. These alcohols subsequently were separated by flash column chromatography to afford compound 22, together with two elimination products, 23 and 24. (Note that with alternative starting materials, a fourth potential product analogous to the regioisomer of 22 would also be expected.) Hydrogenation of compound 22 furnished the desired carbafructofuranose (compound 2); hydrogenation of 23 and 24 also provides sugar analogs (perhaps more properly deoxy sugar analogs) useful in screening for compounds of desired bioactivity, such as enzyme inhibition. Mass spectral and NMR data 20 confirmed the identity of compounds 2, 22, 23 and 24 (Scheme VI).

importantly the preparation of a protected diene system, followed by RCM ring closure, followed by hydroformylation of the protected, highly functionalized cycloalkene intermediate products) is functional with other highly functionalized five- and six-membered cycloalkenes to provide a variety of carbacyclic analogs of naturally occurring sugars and their epimers. Also, the method is functional to produce less highly functionalized cyclic polyols, such as the carba analogs of deoxy sugars or the pentenomycins and their kin, simply by beginning with the appropriate polyol precursor compound. Moreover, libraries of diverse carbacyclic polyols can be produced simply by providing diverse polyol precursor compounds.

EXAMPLE 10

The pentenomycin antibiotics have attracted considerable attention due to their wide range of structural and stereochemical features and biological activities. Pentenomycin was isolated by Umino and co-workers in 1973 from the culture broths of *Streptomyces eurythermus*, while epipentenomycin the C-4 diastereomer, was isolated from carpophores of Perziza sp. There have been several approaches to synthesize these antibiotics and their derivatives however, an expeditious and efficient approach is still needed. Pentenomycin:

A comparison of cyclopentene 8 with pentenomycin indicates that the stereochemistries around the C-4 and C-5 are identical. Therefore, the cyclopentene intermediate 8 was converted to pentenomycin by the following series of reactions: starting compound 8 was treated with BH$_3$:THF to give the corresponding two regioisomeric alcohols; the

Scheme VI

(a) NaBH$_4$, MeOH, 99%, (b) Pd/H$_2$, EtOH, 98%

To date, this is the first reported example of the hydroformylation of a highly functionalized cyclopentene. Using this process, carbacyclic D-fructofuranoside was synthesized in 8 steps with a yield of 36%. This method (including desired alcohol was purified and oxidized by pyridinium chlorochromate to afford the corresponding ketone; the ketone was hydrogenated, then treated with pyridine/acetic anhydride to furnish the acetylated enone; deprotection of the acetate with trifluoroacetic acid/$H_2O$ afforded (−)-pentenomycin. The $^1H$ and $^{13}C$ NMR of the final product was identical with those reported in the literature for (−)-pentenomycin. In summary, a concise and efficient synthesis of the (−)-pentenomycin was demonstrated in 5 steps (46% yield), using the key polyhydroxy cyclopentene intermediate 8.

We claim:

1. A process for synthesizing carbocyclic polyols comprising the steps of:
   (a) subjecting a pentose or a hexafuranose precursor compound that is not protected at the anomeric hydroxyl group to a Wittig reaction to effect ring opening and generate an alkene intermediate product;
   (b) oxidizing the alkene intermediate product of step (a) to yield a keto-alkene intermediate product;
   (c) effecting the nucleophilic addition of vinyl carbanion to the keto-alkene intermediate product of step (b) under Grignard conditions to provide a 1,6-heptadiene product;
   (d) optionally protecting the generated free alcohol of the 1,6-heptadiene product of step (c) to generate a fully protected 1,6-heptadiene product;
   (e) subjecting the 1,6-heptadiene product of step (c) or step (d) to ring closure metathesis (RCM) conditions with an RCM catalyst to effect ring closure and generate a cyclopentene product,
   wherein said pentose or hexafuranose precursor compound is a compound of a formula selected from the group consisting of:

wherein each R is a protecting group independently selected from the group consisting of benzyl, alkylsilyl, benzoyl and acetyl.

2. The process according to claim 1, for synthesizing the functionalized cyclopentene product of step (e), wherein the protecting groups are benzyl such that the pentose precursor compound is 2,3,5-tri-O-benzyl-D-arabinofuranose.

3. The process according to claim 1 for synthesizing the functionalized cyclopentene product of step (e), wherein the ring closing metathesis (RCM) catalyst is chosen from the group consisting of a Schrock's catalyst and a Grubbs' catalyst.

4. The process according to claim 1 for synthesizing a functionalized anhydro cyclopentane product comprising the further step of derivatizing the functionalized cyclopentene product of step (e) by Sharpless epoxidation.

5. A process for synthesizing carbocyclic polyols comprising the steps of:
   (a) subjecting a pentose or a hexafuranose precursor compound that is not protected at the anomeric hydroxyl group to a series of reactions including sequential oxidation, methyl Grignard addition and acetylation followed by thionyl chloride elimination to effect ring opening and generate an alkene intermediate product;
   (b) oxidizing the alkene intermediate product of step (a) to yield a keto-alkene intermediate product;
   (c) effecting the nucleophilic addition of vinyl carbanion to the keto-alkene intermediate product of step (b) under Grignard conditions to provide a 1,6-heptadiene product;
   (d) optionally protecting the generated free alcohol of the 1,6-heptadiene product of step (c) to generate a fully protected 1,6-heptadiene product;
   (e) subjecting the 1,6-heptadiene product of step (c) or step (d) to ring closure metathesis (RCM) conditions with an RCM catalyst to effect ring closure and generate a cyclopentene product,
   wherein said pentose or hexafuranose precursor compound is a compound of a formula selected from the group consisting of:

wherein each R is a protecting group independently selected from the group consisting of benzyl, alkylsilyl, benzoyl and acetyl.

6. A process for synthesizing carbocyclic polyols comprising the steps of:
   (a) subjecting a hexapyranose precursor compound that is not protected at the anomeric hydroxyl group to a Wittig reaction to effect ring opening and generate an alkene intermediate product;
   (b) oxidizing the alkene intermediate product of step (a) to yield a keto-alkene intermediate product;
   (c) (1) providing a 1,7-octadiene product by nucleophilic addition of vinyl carbanion to the keto-alkene intermediate product of step (b) under Grignard conditions or (2) providing a 1,6-heptadiene product by subjecting the keto-alkene intermediate product of step (b) to a Wittig reaction;
   (d) optionally protecting the generated free alcohol of the 1,7-octadiene product of step (c) to generate a fully protected 1,7-octadiene product;
   (e) subjecting the diene product of step (c) or step (d) to ring closure metathesis (RCM) conditions with an RCM catalyst to effect ring closure and generate a functionalized carbocyclic intermediate,
   wherein said hexapyranose precursor compound is a compound of the following formula:

wherein each R is a protecting group independently selected from the group consisting of benzyl, alkylsilyl, benzoyl and acetyl.

7. A process for synthesizing carbocyclic polyols comprising the steps of:
   (a) subjecting a hexapyranose precursor compound that is not protected at the anomeric hydroxyl group to sequential oxidation, methyl Grignard addition, acetylation and thionyl chloride elimination to effect ring opening and generate an alkene intermediate product;

(b) oxidizing the alkene intermediate product of step (a) to yield a keto-alkene intermediate product;

(c) (1) providing a 1,7-octadiene product by nucleophilic addition of vinyl carbanion to the keto-alkene intermediate product of step (b) under Grignard conditions or (2) providing a 1,6-heptadiene product by subjecting the keto-alkene intermediate product of step (b) to a Wittig reaction;

(d) optionally protecting the generated free alcohol of the 1,7-octadiene product of step (c) to generate a fully protected 1,7-octadiene product; and

(e) subjecting the diene product of step (c) or step (d) to ring closure metathesis (RCM) conditions with an RCM catalyst to effect ring closure and generate a functionalized cycloalkene product.

8. A process for synthesizing carbocyclic polyols comprising the steps of:

(a) subjecting a starting compound selected from the group consisting of
  (1) a pentose or a hexafuranose precursor compound and
  (2) a hexapyranose precursor compound to a set of reactions that sequentially effects ring opening and generates an alkene intermediate, oxidixes said alkene intermediate to produce a keto-alkene intermediate, and generates a diene product selected from the group consisting of a 1,6-heptadiene product from the starting compound (1) and a 1,7-octadiene product from the starting compound (2); and (b) subjecting the diene product of step (a) to ring closure metathesis (RCM) conditions with an RCM catalyst to effect ring closure, wherein said pentose or hexafuranose precursor compound is a compound of a formula selected from the group consisting of:

and said hexapyranose precursor compound is a compound of the following formula:

wherein each R is a protecting group independently selected from the group consisting of benzyl, alkylsilyl, benzoyl and acetyl.

9. The process of claim 8, further comprising a step of protecting newly evolved allylic hydroxyls to produce a fully protected diene product of step (a).

10. The process of claim 8 wherein said set of reactions in step (a) comprises a ring opening reaction that effects ring opening and generates an alkene intermediate, said ring opening reaction being selected from the group consisting of (i) a nucleophilic addition of a carbanion under Grignard conditions and (ii) a Wittig reaction.

11. The process of claim 8 wherein said set of reactions in step (a) comprises a diene generating reaction that generates said diene product from said keto-alkene intermediate, said diene generating reaction being selected from the group consisting of (iii) a nucleophilic addition of a carbanion to said keto-alkene intermediate under Grignard conditions to produce said diene product, and (iv) a Wittig reaction that converts said keto-alkene intermediate to said diene product.

12. The process of claim 8, wherein the set of reactions of step (a) comprises
  a Wittig reaction that effects ring opening and generates said alkene intermediate, and
  a Wittig reaction that converts said keto-alkene intermediate to said diene product.

13. The process of claim 8, wherein the set of reactions of step (a) comprises
  a nucleophilic addition of a carbanion under Grignard conditions that effects ring opening and generates said alkene intermediate, and
  a Wittig reaction that converts said keto-alkene intermediate to said diene product.

* * * * *

UNITED STATES PATENT AND TRADEMARK OFFICE
CERTIFICATE OF CORRECTION

PATENT NO. : 6,538,131 B1
DATED : March 25, 2003
INVENTOR(S) : Yousef Al-Abed et al.

It is certified that error appears in the above-identified patent and that said Letters Patent is hereby corrected as shown below:

Column 3,
Line 50, "(Scheme I)" should read -- (Scheme II) --.

Column 4,
Line 13, "Swem" should read -- Swern --.
Line 14, "the" should read -- then --.
Line 16, "furn" should read -- furnished compound --.
Line 34, "1H" should read -- $^1$H --.
Line 40, "syn" should read -- *syn* --.

Column 5,
Line 7, "$^3$C NMR" should read -- $^{13}$C NMR --.
Line 40, "-78° C." should read -- -78° C --.

Column 6,
Line 39, "δ6" should read -- δ --.
Line 53, "20° C." should read -- 20° C --.
Line 63, "δ6" should read -- δ --.
Line 66, "$C_{34}H_{34\ O4}$" should read -- $C_{34}H_{34}O_4$ --.

Column 7,
Line 17, "δ6" should read -- δ --.
Line 21, "δ6" should read -- δ --.
Line 57, "90° C." should read -- 90° C --.

Column 8,
Line 3, "tert-butyl" should read -- *tert*-butyl --.

Column 9,
Line 38, "NMR data 20" should read -- NMR data --.

Column 10,
Line 22, "Perziza sp" should read -- *Perziza sp* --.

UNITED STATES PATENT AND TRADEMARK OFFICE
CERTIFICATE OF CORRECTION

PATENT NO. : 6,538,131 B1
DATED : March 25, 2003
INVENTOR(S) : Yousef Al-Abed et al.

It is certified that error appears in the above-identified patent and that said Letters Patent is hereby corrected as shown below:

Colunms 9-10,
Scheme VI, should read

Column 11,
Lines 32-39, should read

UNITED STATES PATENT AND TRADEMARK OFFICE
CERTIFICATE OF CORRECTION

PATENT NO. : 6,538,131 B1
DATED : March 25, 2003
INVENTOR(S) : Yousef Al-Abed et al.

It is certified that error appears in the above-identified patent and that said Letters Patent is hereby corrected as shown below:

Column 12,
Lines 15-22,  and should read  and

Column 13,
Lines 38-45,  and should read  and

Signed and Sealed this

Ninth Day of September, 2003

JAMES E. ROGAN
*Director of the United States Patent and Trademark Office*